(12) United States Patent
MacDougald et al.

(10) Patent No.: US 6,568,936 B2
(45) Date of Patent: May 27, 2003

(54) METHOD AND APPARATUS FOR PREPARING DENTAL RESTORATIONS

(75) Inventors: Joseph A. MacDougald, Madison, CT (US); Carlino Panzera, Hillsborough, NJ (US)

(73) Assignee: Pentron Laboratory Technologies, LLC.

( * ) Notice: Subject to any disclaimer, the term of this patent is extended or adjusted under 35 U.S.C. 154(b) by 0 days.

(21) Appl. No.: 09/754,887

(22) Filed: Jan. 5, 2001

(65) Prior Publication Data

US 2001/0034010 A1 Oct. 25, 2001

Related U.S. Application Data

(60) Provisional application No. 60/174,543, filed on Jan. 5, 2000.

(51) Int. Cl.$^7$ ................................................. A61C 5/10
(52) U.S. Cl. ........................................ 433/223; 433/214
(58) Field of Search .............................. 433/226, 214, 433/215, 223, 213

(56) References Cited

U.S. PATENT DOCUMENTS

| | | |
|---|---|---|
| 3,861,044 A | 1/1975 | Swinson, Jr. |
| 4,182,312 A | 1/1980 | Mushabac |
| 4,575,805 A | 3/1986 | Moermann et al. |
| 4,837,732 A * | 6/1989 | Brandestini et al. ........ 433/223 |
| 4,935,635 A * | 6/1990 | O'Hara ........................ 433/214 |
| 5,017,139 A | 5/1991 | Mushabac |
| 5,027,281 A | 6/1991 | Rekow et al. |
| 5,092,022 A | 3/1992 | Duret |
| 5,121,333 A | 6/1992 | Riley et al. |
| 5,121,334 A | 6/1992 | Riley et al. |
| 5,128,870 A | 7/1992 | Erdman et al. |
| 5,184,306 A | 2/1993 | Erdman et al. |
| 5,224,049 A | 6/1993 | Mushabac |
| 5,257,184 A | 10/1993 | Mushabac |
| 5,257,203 A | 10/1993 | Riley et al. |
| 5,266,030 A | 11/1993 | Van Der Zel |
| 5,273,429 A | 12/1993 | Rekow et al. |
| 5,343,391 A | 8/1994 | Mushabac |
| 5,372,502 A * | 12/1994 | Massen et al. ............... 433/215 |
| 5,382,164 A * | 1/1995 | Stern .......................... 433/213 |
| 5,440,496 A | 8/1995 | Andersson et al. |
| 5,545,039 A | 8/1996 | Mushabac |
| 5,569,578 A | 10/1996 | Mushabac |
| 5,652,709 A | 7/1997 | Andersson et al. |
| 5,674,073 A | 10/1997 | Ingber et al. |
| 5,690,490 A | 11/1997 | Cannon et al. |

* cited by examiner

Primary Examiner—Cary E. O'Connor
(74) Attorney, Agent, or Firm—Ann M. Knab

(57) ABSTRACT

A method and apparatus for producing dental restorations for teeth that need to be restored. In the process, a first set of data points is retrieved from a tooth or an image of the tooth to be restored. The tooth is prepared by the dentist and a second set of data points is retrieved from the tooth or an image of the tooth. The second set of points is compared to the first set of points to obtain a third set of points. The dental restoration is milled from dental material based on the image resulting from the third set of data points.

9 Claims, 1 Drawing Sheet

METHOD AND APPARATUS FOR PREPARING DENTAL RESTORATIONS

CROSS-REFERENCE TO RELATED APPLICATIONS

This application claims priority to U.S. Provisional Application No. 60/174,543, filed Jan. 5, 2000, which is incorporated herein by reference.

FIELD OF THE INVENTION

The present invention relates generally to a method and apparatus for producing dental restorations using CAM/CAD procedures.

BACKGROUND OF THE INVENTION

A number of methods involving the production of dental restorations and prosthetic devices are known in the art. Generally, a tooth is drilled to remove one or more defects. An impression is taken of the tooth and surrounding teeth. A master model is then created from the impression by pouring a gypsum die material into the cured impression and allowing it to harden. A wax pattern with a sprue is prepared on the die, hardened, removed from the die and invested in a refractory material. The wax is then "burned out" and a refractory pattern is created into which a metal or ceramic material is then cast to provide the desired dental restorative material.

Alternatively, if the lost wax process is not used, a working or duplicate die must be prepared from the original impression or from a duplicate impression made from the master model, both processes involving pouring a refractory into the impression to create the die. Metal or ceramic material is then built onto the die and the die with the material thereon is sintered to provide the dental restoration.

The above procedures are time consuming and often costly due to laboratory fees. Computer assisted design and milling machines have been introduced in the industry and are starting to make an impact. Although many of the above-mentioned steps may be reduced with the computer assisted tools, there remains a need to further simplify the processes. U.S. Pat. No. 5,690,490 is directed to a method and apparatus for fabrication of a dental restoration by pinhead molding. The method requires that impressions be taken and placed in a laser scanning box, wherein laser scanning is conducted within a controlled environment. The process is time consuming in that it requires two sets of impressions to be taken and thereafter scanned.

It is desirable that dental restorations be formed from images taken directly from the mouth. It is preferable that the restorations duplicate the original shape of the restored tooth as closely as possible.

SUMMARY OF THE INVENTION

These and other objects and advantages are accomplished by a method of producing dental restorations for teeth that need to be restored. In the process, a first set of data points is retrieved from a tooth or an image of the tooth to be restored. The tooth is prepared by the dentist and a second set of data points is retrieved from the tooth or an image of the tooth. The second set of points is compared to the first set of points to obtain a third set of points. The dental restoration is milled from dental material based on the image resulting from the third set of data points.

In an apparatus herein, a scanning device such as a probe is provided to scan the tooth or teeth in the patient's mouth or an image produced from the tooth or teeth in the patient's mouth to provide data that represents the scanned teeth. The apparatus further includes a mechanism for comparing two sets of data from the scanning device and calculating a third set of data. The apparatus may include a machining device or the machining device may be a separate device. The machining device reads and interprets the third set of data and mills dental material, such as metal or ceramic material, into a dental restoration representative of the image provided from the third set of data points.

The apparatus produces a three-dimensional body that is a dental restoration such as an orthodontic appliance, bridge, space maintainer, tooth replacement appliance, splint, crown, partial crown, denture, post, tooth, jacket, inlay, onlay, facing, veneer, facet, implant, abutment, cylinder, or connector.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
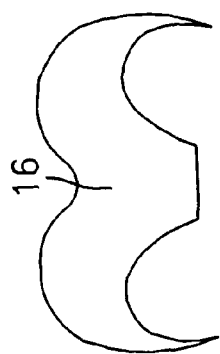
FIG. 1 is a schematic diagram of the representations achieved from the various sets of data in the manufacture of an inlay in accordance with the process herein.
Figure 1:
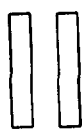
Figure 1:
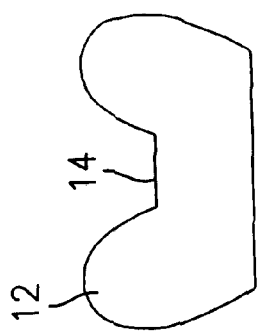
Figure 1:
Figure 1:
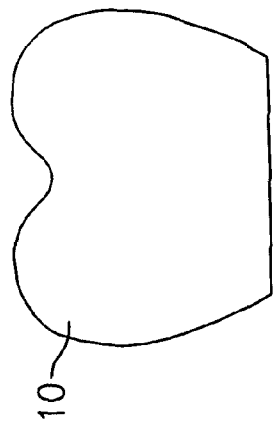

As will be appreciated, the present invention provides a method for producing dental restorations that closely resemble the original contour and shape of the tooth or teeth prior to the occurrence of decay or damage thereto. FIG. 1 schematically illustrates the steps undertaken to achieve the final restoration. In FIG. 1, a tooth 10 is to be fitted for an onlay. A scanning device such as a probe is moved along tooth 10 to obtain a set of data that represents the three-dimensional contour and shape of tooth 10. Any currently available scanning or data gathering device may be used such as those set forth in U.S. Pat. Nos. 4,182,312, 4,575,805, 5,257,184, 5,343,391, 5,454,039, and 5,569,578, all of which are hereby incorporated by reference. Optionally, photographs may be taken or a model may be produced of the tooth to be treated. The photographs or model are then converted into a set of data that represents the contour and shape of the tooth. In all methods, the data is collected on the tooth prior to any preparation of the tooth.

Figure 2:
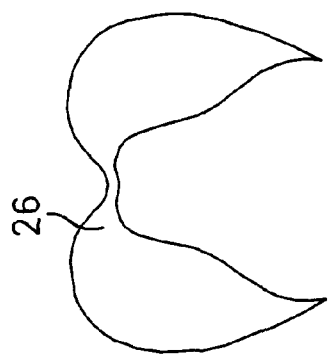
FIG. 2 is a schematic diagram of the representations achieved from the various sets of data in the manufacture of a crown in accordance with the process herein.
Figure 2:
Figure 2:
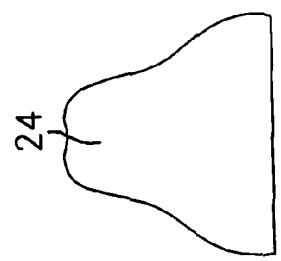
Figure 2:
Figure 2:
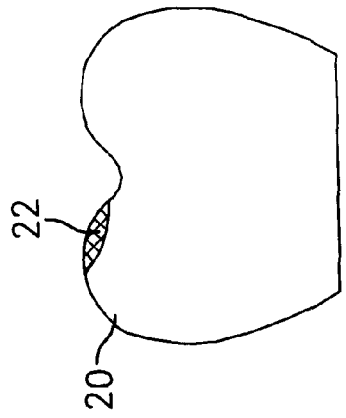

Frequently, the tooth to be treated already has some defects thereon which change the original shape of the tooth. FIG. 2 shows a tooth 20 having a defect 22 thereon. In such a case, the same tooth in the adjacent quadrant is used as the "target" tooth to obtain the data corresponding to the contour and shape of the tooth. Alternately, the damaged tooth may be used as the target tooth, but the data obtained will then be modified to correct the defects thereon. This may be performed by using a computer to "build up" that section of the tooth which is damaged to provide a profile that represents a fully restored or original, unaltered tooth. If there is a missing tooth which needs a restoration, data may be obtained from the adjacent teeth, the same tooth in the adjacent quadrant, and occlusion teeth to provide an image most similar to the missing tooth. The tooth in the adjacent quadrant will provide the overall general shape. The adjacent teeth will assist in providing the contour and shape of the proximal surfaces of the missing tooth and the occlusion teeth will assist in providing the contour of the occlusal surface of the teeth.

The accumulation of the data points corresponding to the original tooth will provide the information necessary to form the external surface of the restoration. Any sensing or scanning device may be used to perform this step such as an optical scanner, a probe scanner, a laser scanner or a tactile scanner.

After all of the material data regarding the original tooth has been collected, the tooth may be prepared by the dentist. This may include removing the damaged part of the tooth which may involve removing the enamel and dentition from the tooth. FIGS. 1 and 2 show prepared teeth 12 and 24. Tooth 12 has been prepared by removing material from the upper middle area of the tooth and forming a groove 14 therein. More area was needed to be removed from tooth 24 which represents a small tooth stump. After the dentist has prepared the tooth, the prepared tooth is scanned for contour and shape to obtain a set of data points which represents the three-dimensional contour and shape of the prepared tooth. This set of data is used to form the internal surface or inside of the restoration which attaches to the tooth in the mouth.

The set of points obtained from the original tooth (first set of points) and the set of points obtained from the prepared tooth (second set of points) are compared to obtain a set of points (third set of points) which provides the shape of the restoration to be fabricated. Mathematically, the data from the prepared tooth is subtracted from the data of the original tooth to provide data which forms an image which image is then used to fabricate the restoration used to restore the prepared tooth to the shape of the original tooth, or more precisely, the restoration will fit onto the prepared tooth to provide a tooth which mimics the original tooth.

FIGS. 1 and 2 show restorations 16 and 26, respectively, which are formed from the result obtained by subtracting the prepared tooth data from the original tooth data. The data obtained from this equation is used to create the restoration. The restoration may be machined by any suitable technique, including electro-erosion, laser cutting, ultrasonic material removal, milling, grinding and/ or drilling such as those techniques set forth in U.S. Pat. Nos. 5,121,333 and 5,184, 306, which are hereby incorporated by reference. The material used to fabricate the restoration may be any suitable dental material including alloys, metals, composites, ceramics and glass-ceramics.

The interior of the restoration may be reduced in size in order to allow for adhesive materials, such as luting and bonding materials, to be applied to the interior of the restoration prior to insertion on the tooth. This may be performed prior to fabrication by reducing the size of the interior using the computer. The process herein may utilize computer assisted design and computer assisted milling techniques and equipment which are adapted to perform the steps of the invention.

In the apparatus herein, a scanning device such as a probe is provided to scan the tooth or teeth in the patient's mouth or to scan an image produced from the tooth or teeth in the patient's mouth to provide data that represents the scanned teeth. The apparatus further includes a computer for comparing two sets of data received from the scanning device and calculating an error function between the first and second set of data to provide a third set of data. The apparatus may include a machining device or the machining device may be a separate device. The machining device reads and interprets the third set of data and mills dental material, such as metal or ceramic material, into a dental restoration representative of the image provided from the third set of data points.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for producing a three-dimensional body comprising:

scanning a first tooth to obtain a first set of data;

preparing a second tooth;

scanning the prepared tooth to obtain a second set of data;

calculating the difference between the first set of data and the second set of data to obtain a third set of data;

producing a three-dimensional body from the third set of data.

2. The method of claim 1 wherein the first tooth is a target tooth which provides a model of an original shape of the second tooth.

3. The method of claim 2 wherein the preparing step comprises reducing the enamel on the tooth.

4. The method of claim 3 wherein the preparing step further comprises reducing the dentition on the tooth.

5. The method of claim 2 wherein the scanning steps comprise using a scanner selected form a probe scanner, a tactile scanner and an optical scanner.

6. The method of claim 2 wherein the producing step comprises using a technique selected from electro-erosion, laser cutting, ultrasonic material removal, milling, grinding and drilling to create the three-dimensional body.

7. The method of claim 2 wherein the three-dimensional body is a restoration selected from an orthodontic appliance, bridge, space maintainer, tooth replacement appliance, splint, crown, partial crown, denture, post, tooth, jacket, inlay, onlay, facing, veneer, facet, implant, abutment, cylinder, and connector.

8. A restoration prepared by the method comprising:

scanning a first tooth to obtain a first set of data;

preparing a second tooth;

scanning the prepared tooth to obtain a second set of data;

calculating the difference between the first set of data and the second set of data to obtain a third set of data;

producing the restoration from the third set of data.

9. The restoration of claim 8 selected from an orthodontic appliance, bridge, space maintainer, tooth replacement appliance, splint, crown, partial crown, denture, post, tooth, jacket, inlay, onlay, facing, veneer, facet, implant, abutment, cylinder, and connector.

* * * * *

UNITED STATES PATENT AND TRADEMARK OFFICE
CERTIFICATE OF CORRECTION

PATENT NO. : 6,568,936 B2  
DATED : June 13, 2003  
INVENTOR(S) : Joseph A. MacDougald and Carlino Panzera It is certified that error appears in the above-identified patent and that said Letters Patent is hereby corrected as shown below:

<u>Title page,</u>
Item [73], Assignee, delete the Assignee "Pentron Laboratory Technologies, LLC" and replace with -- Jeneric/Pentron Incorporated --.

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,568,936 B2
DATED         : December 9, 2003
INVENTOR(S)   : Joseph A. MacDougald and Carlino Panzera It is certified that error appears in the above-identified patent and that said Letters Patent is hereby corrected as shown below:

Column 1,
Lines 13 and 14, delete "CAM/CAD" and replace with -- CAD/CAM --.

Signed and Sealed this

Third Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,568,936 B2  Page 1 of 1
DATED : May 27, 2003
INVENTOR(S) : Joseph A. MacDougald and Carlino Panzera It is certified that error appears in the above-identified patent and that said Letters Patent is hereby corrected as shown below:

Column 1,
Lines 13 and 14, delete "CAM/CAD" and replace with -- CAD/CAM --.

Signed and Sealed this

Twenty-fourth Day of February, 2004

JON W. DUDAS
*Acting Director of the United States Patent and Trademark Office*